United States Patent [19]

Goodwin

[11] 4,244,713
[45] Jan. 13, 1981

[54] APPARATUS FOR ANALYSIS OF ABSORBED GASES

[75] Inventor: Brian Goodwin, Neston, England

[73] Assignee: The Medishield Corporation Limited, London, England

[21] Appl. No.: 935,064

[22] Filed: Aug. 18, 1978

[30] Foreign Application Priority Data

Aug. 25, 1977 [GB] United Kingdom ............... 35633/77

[51] Int. Cl.³ ............................................. B01D 53/22
[52] U.S. Cl. ....................................... 55/158; 55/270; 73/19; 128/632
[58] Field of Search ............... 55/16, 158, 270; 73/19, 73/23, 23.1; 128/2 G, 2 L, 2.05 R; 356/39, 74; 422/68, 98; 210/490, 506, DIG. 6

[56] References Cited

U.S. PATENT DOCUMENTS

| 3,413,777 | 12/1968 | Langley et al. | 55/158 |
| 3,499,265 | 3/1970 | Langley et al. | 55/158 |
| 3,673,864 | 7/1972 | Cubberly, Jr. | 73/19 X |
| 3,751,879 | 8/1973 | Allington | 55/158 |
| 3,803,810 | 4/1974 | Rosenberg | 55/159 |
| 3,828,527 | 8/1974 | Briggs et al. | 55/158 |
| 3,911,080 | 10/1975 | Mehl et al. | 55/158 X |
| 3,952,730 | 4/1976 | Key | 128/2 L X |
| 4,058,373 | 11/1977 | Kurz et al. | 55/158 X |

*Primary Examiner*—Robert H. Spitzer
*Attorney, Agent, or Firm*—Dennison, Dennison, Meserole & Pollack

[57] ABSTRACT

A gas permeable probe for use in the analysis of absorbed gases in liquids, notably in the blood, by mass spectroscopy, comprises a flexible plastics capillary tube fitted at one end with a plug of porous material and covered with a protective layer of polymeric material. The gas permeability of the porous plug is substantially less than that of the polymeric layer so that it is the plug which defines the gas flow from the liquid under test into the tube when the tube is evacuated.

6 Claims, 2 Drawing Figures

APPARATUS FOR ANALYSIS OF ABSORBED GASES

FIELD OF THE INVENTION

The present invention relates to a device for use in the analysis of absorbed gases in liquids, by mass spectroscopy. More particularly, the present invention relates to a gas permeable probe fo use in the analysis of absorbed gases in liquids, notably in the blood, by mass spectroscopy.

BACKGROUND OF THE INVENTION

Devices at present in use for the analysis of absorbed gases, for example in the blood, utilise a gas permeable membrane manufactured from a polymeric material. This gas permeable membrane is mounted at one end of a flexible capillary tube which is connected, at its other end, directly to the analysis chamber of a mass spectrometer. Gases diffusing across the permeable membrane pass into the evacuated interior of the capillary and so to the mass spectrometer for analysis.

The devices at present in use suffer from a number of disadvantages, some of which are:

1. The permeability of polymers differs significantly for each gas species. Because of this, certain operation modes for the mass spectrometer/probe system, which can give greater accuracy and stability, are precluded when a polymeric membrane is employed.

2. The activation energy of diffusion is relatively high for polymer materials so that significant changes in permeability can occur over a temperature range of only a few degrees. Correction for temperture changes is difficult since the activation energy is different for each component of the diffusant gas.

3. The devices are subject to variations in the permeability of the polymeric membrane due to wetting of the surface, deposition of substances, for example protein and other particular contaminants, and to physical deformation of the polymer resulting from the absorption of water vapour (in the in vivo case).

By practice of the present invention, one or more of the above disadvantages may be overcome or substantially eliminated.

SUMMARY OF THE INVENTION

According to the present invention there is provided a device for use in the analysis of absorbed gases in liquids, which comprises a flexible plastics material tube, one end of the tube being fitted with a porous material plug having a permeability which in use defined the passage of gas through said end of the tube, and the end of the tube being covered with a protective polymeric material layer. The gas flow into the tube from the liquid, for example when the tube is evacuated, is defined by the permeability of the porous material plug. That is, the permeability of the porous plug is less, preferably substantially less than the permeability of the protective polymeric material layer.

The device according to the present invention is particularly useful in the analysis of absorbed gases in blood, for example for in vivo measurements of gas tension in arterial and venous blood, but may be used in the analysis of absorbed gases in any liquid, by mass spectroscopy. Using the technique of mass spectroscopy, the capillary tube will be evacuated and the gas flow into the evacuated capillary will be defined by the plug of porous material.

Suitable flexible plastics material tubes are impermeable capillary tubes of, for example, a polyester material, saran (polyvinylidene), Mylar, or nylon. A coating of, for example dacron, may be provided on the outer or inner surface of those flexible plastics material tubes which comprise hydrophilic materials such as nylon. This reduces the ingress of water vapour through the capillary wall.

The porous material plug has a low gas permeability, for example $10^{-8}$ to $10^{-10}$ liters/sec and may be of a material such as, for example, sintered materials such as sintered noble metals, silicon carbide, glass, a ceramic or a poroplastic. When a pressure gradient exists across the porous material plug the permeability of the porous material plug, to the components of an absorbed compound gas, is proportional to $M^{-\frac{1}{2}}$ where M is the mass of the diffusant molecule. The components in the gas mixture which has diffused through the porous material plug will therefore be representative of the gases dissolved in the sample being tested. When the device according to the present invention is used in the analysis of absorbed gases in blood, the preferred permeability of the porous material plug is $10^{-8}$ to $10^{-10}$ liters/sec.

The polymeric material covering the end of the flexible plastics material tube should have a permeability substantially greater than that of the porous material plug. For example, it may have a gas permeability of approximately 10 to 100 times that of the porous material plug. A suitable material for the polymeric material layer is hydrophobic polypropylene.

In order to avoid the formation of voids between the porous material plug and the flexible plastics material tube, an interlayer of glass or epoxy resin may be provided between these two materials. A glass interlayer may be provided by melting glass onto a ceramic or sintered plug to form a coating, and then inserting the glass coated plug into the end of the flexible plastics material tube and melting the plastics tube onto the glass coated plug.

The polymeric material layer may be applied to the end of the flexible plastics material tube by a dipping process, or by fixing a preformed sheath. Further, the purpose of the polymeric material layer is to constrain the diffusion of molecules of liquid which may impair the gas permeability of the porous plug and to inhibit the passage of water vapour from the liquid into the gas space within the flexible plastics material tube.

For in vivo applications of the device according to the present invention, the polymeric material layer should be hydrophobic.

The diameter of the flexible plastics material tube is typically approximately 1/16th of an inch and typically has a wall thickness of approximately 10 thousandths of an inch. This results in an overall diameter for the porous material plug of approximately 40 thousandths of an inch. However, internal diameters for the flexible plastics material tube down to approximatly 20 thousandths of an inch have been utilised and the size of the tube actually utilised will depend on the particular application to which it is to be placed.

In an alternative embodiment of the present invention a filler material is provided between the polymeric material layer and the porous material plug. This filler material should have a substantially higher gas permeability than the porous material plug. The purpose of the filler material is to aid in the contouring of the tip of the device during manufacture. The filler material may be laminated PTFE (polytetrafluoroethylene).

The useful range of permeability for a device according to the present invention is limited by the rate of gas transport to the device tip from the bulk fluid, and by the mass spectrometer sensitivity. If gas permeability through the porous material plug is so high that the gas lost by diffusion through the porous material plug cannot be replaced by diffusion from the bulk fluid then, in the absence of other transport mechanisms such as fluid movement, a region depleted of dissolved gas forms about the tip of the device.

A gas permeability for the porous material plug giving a gas flow of $10^{-8}$ cm$^3$ sec$^{-1}$ is suitable for measurements of dissolved gas in water having a minimum flow velocity of 5 cm/sec.

BRIEF DESCRIPTION OF THE DRAWINGS

The invention will now be more particularly described, by way of example, with reference to the accompanying drawings, in which.

DESCRIPTION OF THE PREFERRED EMBODIMENTS

Figure 1:
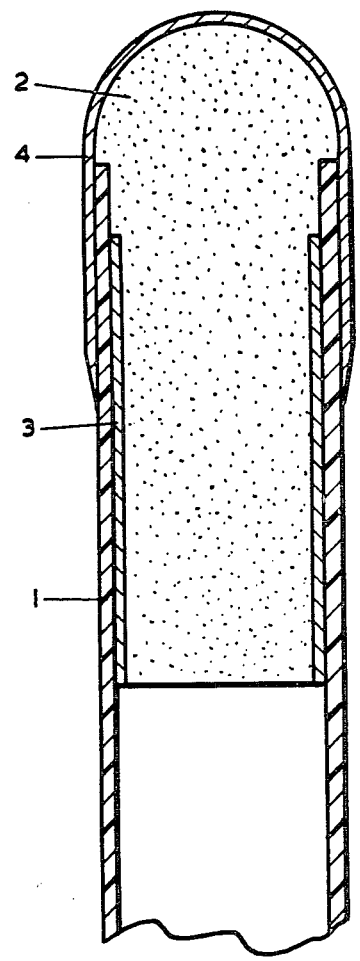
FIG. 1 is a sectional view of a first embodiment of a device in accordance with the invention.

Referring to FIG. 1, there is shown a flexible plastics material capillary tube 1 having inserted in one end thereof a porous material plug 2. Interposed between the plug 2 and tube 1 is a glass interlayer 3. The exposed, domed surface of the plug and the end of the tube are covered by a protective layer 4 of polymeric material. The manner of use of the device in the analysis of absorbed gases in liquids, the relative gas permeabilities of the plug 2 and layer 4, and the choice of materials from which the tube 1, plug 2 and layer 4 are manufactured are all in accordance with the examples hereinbefore mentioned.

Figure 2:
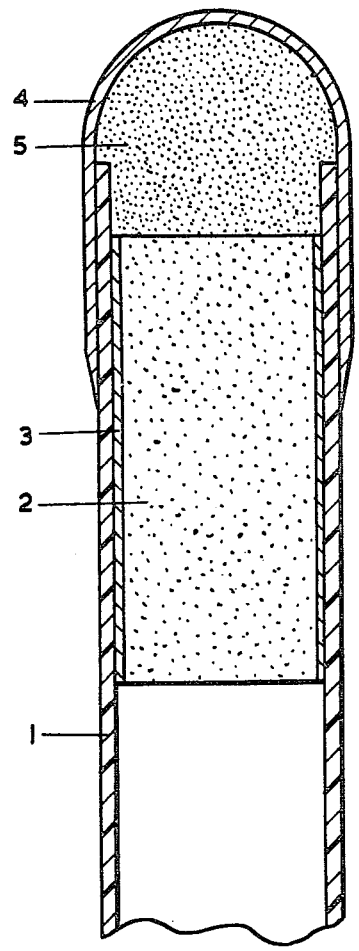
FIG. 2 is a similar view of a second embodiment of a device in accordance with the invention.

Turning to FIG. 2, this shows a second device of a construction similar to that shown in FIG. 1, except that in this case the porous material plug 2 terminates within the end of the tube 1 and a second plug 5 of a filler material having a gas permeability substantially higher than that of the plug 2 is provided between the plug 2 and the protective polymeric material layer 4.

I claim:

1. A device for use in the analysis of absorbed gases in liquids, comprising a flexible plastics material tube, one end of which is fitted with a porous material plug having a permeability which in use defines the passage of gas through said end of the tube, and the end of the tube being covered with a polymeric material layer for protecting said porous plug by constraining the diffusion of liquid as would impair its gas permeability, said polymeric layer also inhibiting the passage of water vapor through said porous plug, the gas permeability of the porous material plug being substantially less than that of the polymeric material layer.

2. A device according to claim 1 wherein the gas permeability of the polymeric material layer is in the range of 10 to 100 times that of the porous material plug.

3. A device according to claim 1 wherein the gas permeability of the porous material plug is in the range of $10^{-8}$ to $10^{-10}$ liters/second.

4. A device according to claim 1 comprising an interlayer of glass or epoxy resin provided between the porous material plug and flexible tube.

5. A device according to claim 1 comprising a plug of filler material provided between the porous material plug and the polymeric material layer, the gas permeability of the filler material plug being higher than that of the porous material plug.

6. A device according to claim 1 wherein the porous material plug is manufactured from a material chosen from the group comprising sintered noble metals, silicon carbide, glass, ceramics, and poroplastics.

* * * * *